United States Patent [19]
Altman

[11] Patent Number: 5,507,779
[45] Date of Patent: Apr. 16, 1996

[54] CARDIAC INSULATION FOR DEFIBRILLATION

[75] Inventor: Peter A. Altman, Woodside, Calif.

[73] Assignee: Ventritex, Inc., Sunnyvale, Calif.

[21] Appl. No.: 226,742

[22] Filed: Apr. 12, 1994

[51] Int. Cl.$^6$ ................................................. A61N 1/39
[52] U.S. Cl. ........................... 607/5; 607/63; 128/908; 128/897
[58] Field of Search .................................. 607/5, 63, 96, 607/113, 129; 128/908, 897, 899; 600/37; 601/153

[56] References Cited

U.S. PATENT DOCUMENTS

| | | | |
|---|---|---|---|
| 3,034,501 | 5/1962 | Hewson | 601/153 |
| 3,983,863 | 10/1976 | Janke et al. | 600/37 |
| 4,605,006 | 8/1986 | Jacques | 607/113 |
| 4,676,790 | 6/1987 | Kern | 623/5 |
| 4,947,843 | 8/1990 | Wright et al. | 607/96 |
| 5,044,374 | 9/1991 | Lindemans et al. | |
| 5,249,574 | 10/1993 | Bush et al. | 607/9 |
| 5,290,299 | 3/1994 | Fain et al. | 606/142 |

OTHER PUBLICATIONS

"Defibrillation Threshold Measurements Using an Endocardial Head Configuration with and without Inactive Epicardial Patch in Days", Callihan et al., Circulation, vol. 88, No. 4, Part 2, Oct. 1993, pp I-592, No. 3185.

"Comparison of Defibrillation Probability of Success Curves for an Endorcardial Lead Configuration With and Without an Inactive Epicardial Patch" Callihan, et al., *JACC*, vol. 25, No. 6, May 1995:1373-9.

"Cardiac Compression Significantly Improves Defibrillation Efficacy", Salim F. Idriss, et al., Circulation, vol. 88, No. 4, Part 2, Oct. 1993, pp. I-592 No. 3186.

"ICD Implantation via Thoracoscopy without the Need for Sternotomy or Thoractomy", Howard Furmin, et al., PACE, vol. 16, Feb. 1993, pp. 257-260.

"Improved Internal Defibrillation Efficacy with a Biphasic Waveform", Eric S. Fain, et al., American Heart Journal, vol. 117, No. 2, Feb. 1989, pp. 358-364.

"Current Concepts for Selecting the Location, Size and Shape of Defibrillation Electrodes", Raymond E. Ideker, et al., PACE, vol. 14, Feb. 1991, Part I, pp. 227-240.

*Primary Examiner*—William E. Kamm
*Assistant Examiner*—Jeffrey R. Jastrzab
*Attorney, Agent, or Firm*—Steven M. Mitchell; M. Elizabeth Bush; Mark J. Meltzer

[57] ABSTRACT

A defibrillation insulating device insulates the heart from the body. This forces current to flow through the heart without passing through surrounding tissues, thus increasing the current density throughout the heart, to depolarize the majority of the cardiac tissue with a minimum of energy.

25 Claims, 3 Drawing Sheets

CARDIAC INSULATION FOR DEFIBRILLATION

FIELD OF THE INVENTION

The present invention relates generally to cardiac defibrillation devices, and more specifically to an implantable device which provides a means for directing energy to the heart during defibrillation.

BACKGROUND OF THE INVENTION

It is desirable to reduce the size of an implantable cardioverter/defibrillator (ICD) in order to improve patient comfort, reduce risk of erosion through the skin, and facilitate pectoral placement. Because the batteries and capacitors account for a large portion of the defibrillator, reducing the defibrillation threshold (DFT), or the amount of energy required to defibrillate the heart, is key to allowing the device size to be reduced. Using less energy to defibrillate has the added benefit of improving patient comfort and reducing trauma to the conduction system.

Many techniques have been used in the past to reduce DFTs. These include the use of modified electrodes, described by Ideker et al. in "Current Concepts for Selecting the Location, Size and Shape of Defibrillation Electrodes," *PACE* 1991, 14:227–240, and the use of biphasic waveforms, described by Fain et al. in "Improved Internal Defibrillation Efficacy with a Biphasic Waveform," *American Heart Journal* 1989, 117:358–364.

SUMMARY OF THE INVENTION

The invention comprises an epicardial insulation device for use during electrical stimulation of the heart having the ability to direct energy to the heart while minimizing the energy delivered to surrounding tissue. This device may be used with various combinations of transvenous, epicardial, or subcutaneous electrodes. By substantially limiting energy delivery to only cardiac tissue, the energy required for defibrillation can be minimized, since energy is not shunted to surrounding tissue. As used herein, the term "epicardial" will be used to refer to either epicardial (in the pericardial space) or pericardial (on the pericardium, or extrapericardial).

Epicardial insulation prevents current flow to the tissues surrounding the heart, forcing the current to pass through the heart muscle and contained blood, which increases localized current density, thus lowering defibrillation thresholds. The system impedance increases with epicardial insulation due to the fewer current pathways, but energy is not wasted in noncardiac tissues. In fact, the rise in impedance introduced by the insulation is an indication of the advantage being provided.

Combining insulation with a transvenous lead system that incorporates a subcutaneous patch electrode requires that a portion of the heart not be insulated. In one embodiment of the invention, the controlled creation of a window in the insulation acts to direct tho energy from the transvenous electrodes to the subcutaneous patch electrode such that the current follows the path of choice. For example, to deliver more energy to the apex of the left ventricle, a hole or opening in the insulation of approximately 1.5 inches in diameter at that location acts effectively as an electrode placed in that region.

The insulation is of flexible, nonabrasive, biocompatible material, such as expanded polytetrafluoroethylene (PTFE) or silicone rubber, and of sufficient thickness and dielectric strength to provide adequate electrical insulation from the local potential gradient. The material is provided with a shape so that when formed to the heart, it partially or fully surrounds the heart, and conforms to the epicardium. The material is preferably of an elastomeric material and sufficiently thin and compliant such that it can stretch and contract with the filling and pumping of the heart.

In an alternative embodiment, a biocompatible material is injected into the pericardial space in liquid or gel form for less invasive delivery. The material has a lower conductivity than surrounding body tissue, to limit the current flow to the body. One such material is collagen glue, which may be used alone, or may be mixed with silicone rubber particles to increase the insulative effect.

It is not intended that the device seal the heart from surrounding tissue or be without perforations, but the effectiveness of the device for directing energy to the heart generally increases with increasing coverage.

By directing current flow through the heart with the insulation device, the defibrillation electrode(s) may be reduced in size to eliminate current shunting while maintaining the lower DFT found with larger electrodes. For an epicardial electrode, this reduction in surface area has the advantage of allowing the electrode to be more easily rolled as required for less invasive implantation through a limited thoracotomy or through a trocar, with or without the aid of a thoracoscope. For a transvenously placed lead, this reduction in surface area may allow the overall lead diameter to be reduced, so that a smaller diameter lead introducer is required to insert the lead through the vein.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
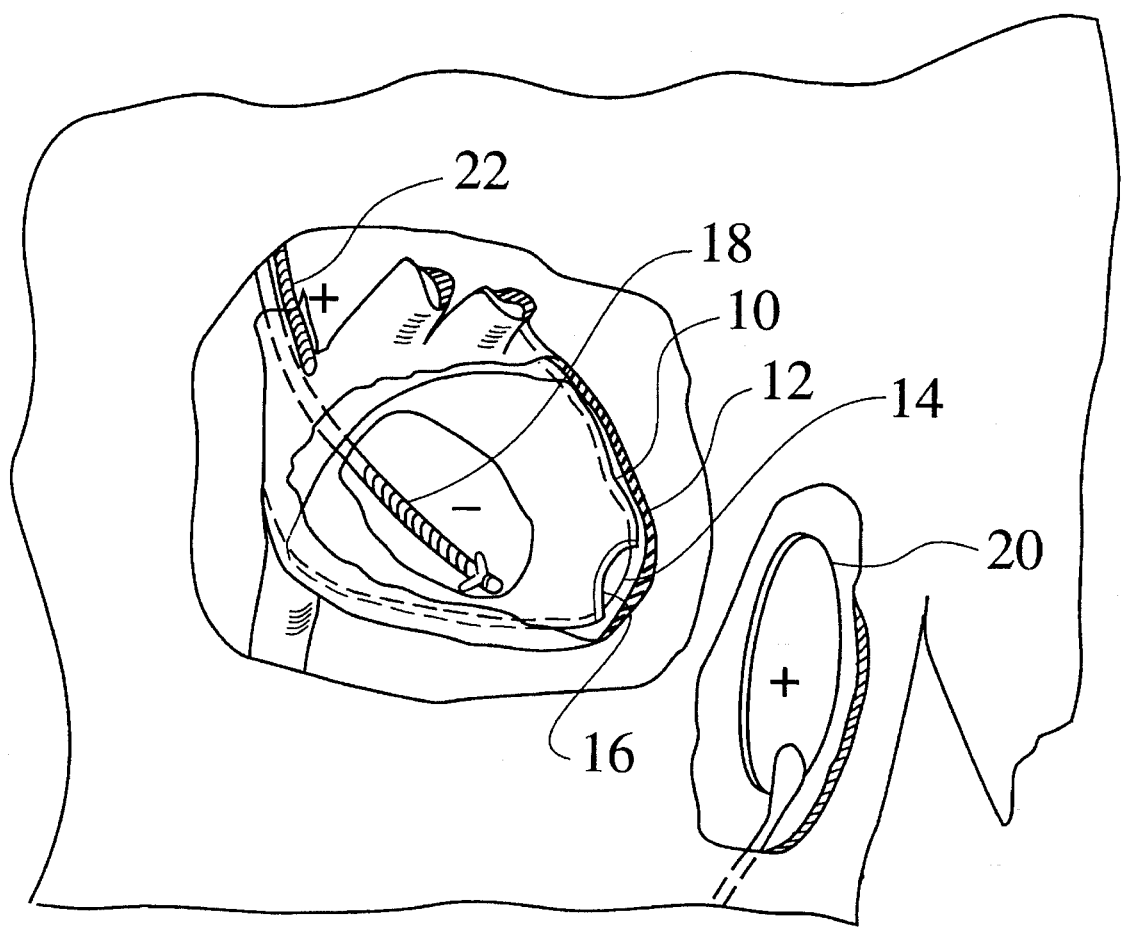
FIG. 1 shows an insulation device in position in the pericardial space of a patient's heart.

FIG. 1 shows an insulation device 10 in position in the pericardial space of a patient's heart. Pericardium 12 and epicardium 14 of the heart are shown, with the pericardial space defined as the space between them. Insulation device 10 has a window, or aperture, 16, which allows current to flow from a transvenously positioned right ventricular (RV) electrode 18 to a subcutaneous (SQ) electrode 20. Window 16 is about two to five centimeters in width, and is preferably eccentric with respect to the edge of the insulation device to provide flexibility of orientation to the implanting physician. The implanted position of window 16 ensures that current flowing between the electrodes is directed through the apex of the heart. To complete the defibrillation electrode system, a superior vena cava (SVC) electrode 22 is positioned in or near the SVC, and is of the same polarity as the SQ electrode. Alternatively, a single transvenous electrode, either RV or SVC, may be used. As another alternative, the SVC and SQ electrodes may be opposite in polarity.

There may be several regions of the heart where insulation is unnecessary or not preferred for a number of reasons. For a current field developed in the heart for a given set of electrodes, there will be regions where insulation will not provide significant advantage by limiting current shunting. By leaving these regions of the heart uninsulated, a current pathway can be provided for transthoracic defibrillation. Any region may be left open as desired. Transvenous electrodes may be configured along with epicardial insulation to optimize localized advantages of cardiac insulation, while simultaneously providing a clear pathway for external, transthoracic defibrillation or for subcutaneous defibrillation. The material may be planar, or may be nonplanar, such as formed in a cup shape to conform to the heart. Several sizes may be offered to provide optimal fit to the patient's heart. Alternatively, the material may be manufactured larger than intended for implant, to be trimmed to fit the heart by the implanting physician.

The insulation can be inserted into the appropriate location through a trocar, using a similar technique as that used to introduce a defibrillation electrode, as described by Frumin et al. in "ICD Implantation via Thoracoscopy without the Need for Sternotomy or Thoracotomy," in PACE, Vol. 16, February 1993, pp. 257–260. Alternatively, the insulation device may be introduced during other surgery such as coronary artery bypass graft (CABG) surgery. The insulation may be fixated to the myocardium, or to the pericardium using the "Double Jaw Apparatus for Attaching Implanted Materials to Body Tissue," described by Fain et al. in U.S. Pat. No. 5,290,299, or using the technique described by Bush et al. in "Implantation of Leads," U.S. Pat. No. 5,249,574, which are both assigned to the assignee of the present application and are incorporated herein by reference.

Figure 2:
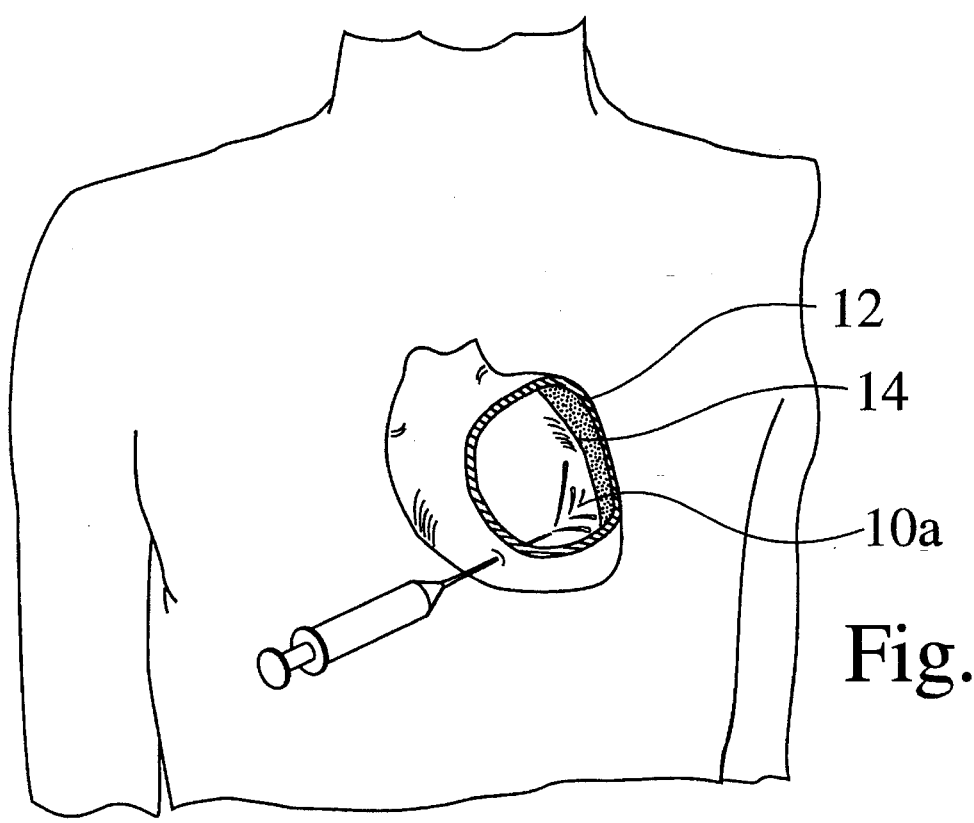
FIG. 2 shows an insulation device being injected into the pericardial space of a patient's heart.

FIG. 2 shows an alternative embodiment of an insulation device 10a in a liquid or gel form being injected into the pericardial space of a patient's heart 14. This biocompatible material is selected to have a lower conductivity than surrounding body tissue, to limit the current flow to the body. The liquid form may be an uncured state of the insulation material, which may cure into a compliant, solid form following injection. Alternatively, a glue may be used wherein water is absorbed by the surrounding tissue to allow the glue to set. A collagen glue may be used, either alone or mixed with silicone rubber particles, PTFE particles, or other insulative particles, to increase the insulative effect.

Figure 3:
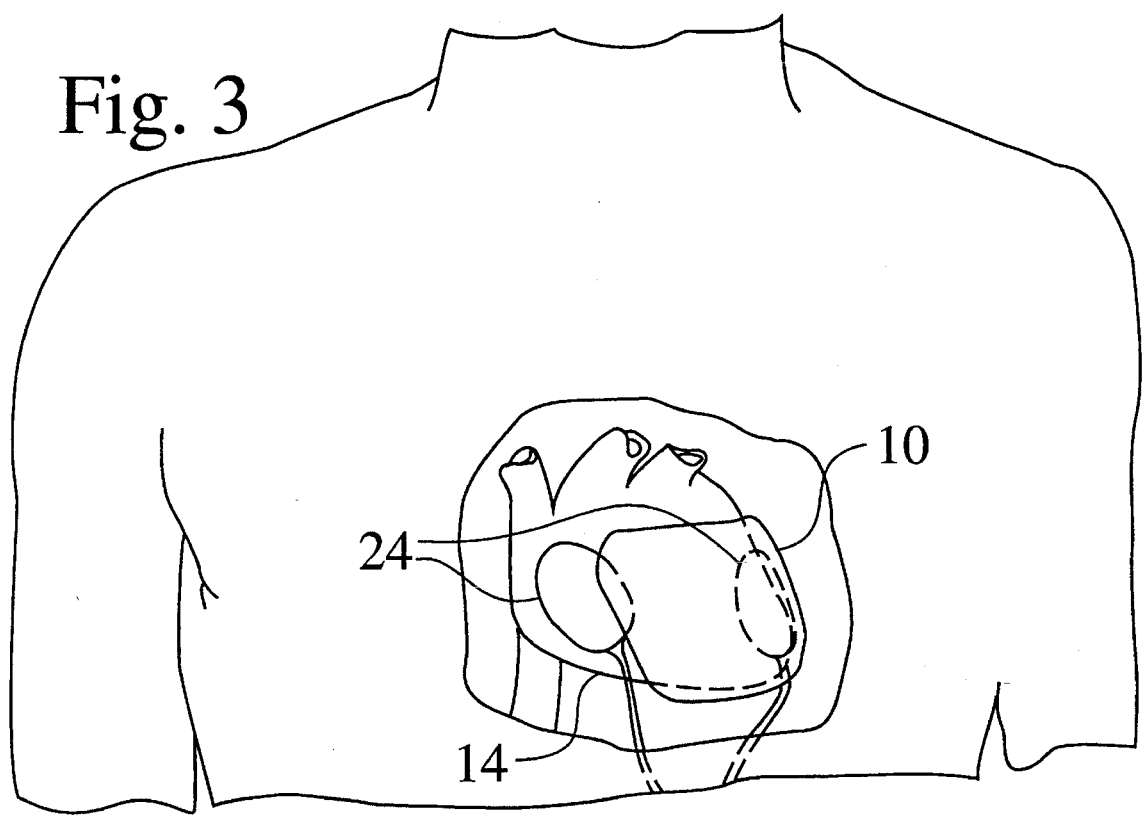
FIG. 3 shows an insulation device used with two epicardial electrodes.

FIG. 3 shows an insulation device 10 used with two epicardial electrodes 24. The insulation device is shown to cover only a portion of the heart 14, and prevents current shunting from electrode to electrode through noncardiac tissue. Alternatively, device 10 may be larger to cover substantially all of heart 14. As another alternative, if the path of greatest current shunt is identifiable, device 10 may be made smaller to interrupt only this path. By making the epicardial insulation smaller, the surgery to implant it will be less invasive. The pericardium is not shown in FIG. 3. Epicardial electrodes 24 are always used between the epicardial surface of the heart and insulation device 10; however, electrodes 24 may be located in the pericardial space or extrapericardially or one of each, and insulation device 10 may be located in the pericardial space or extrapericardially.

Figure 4:
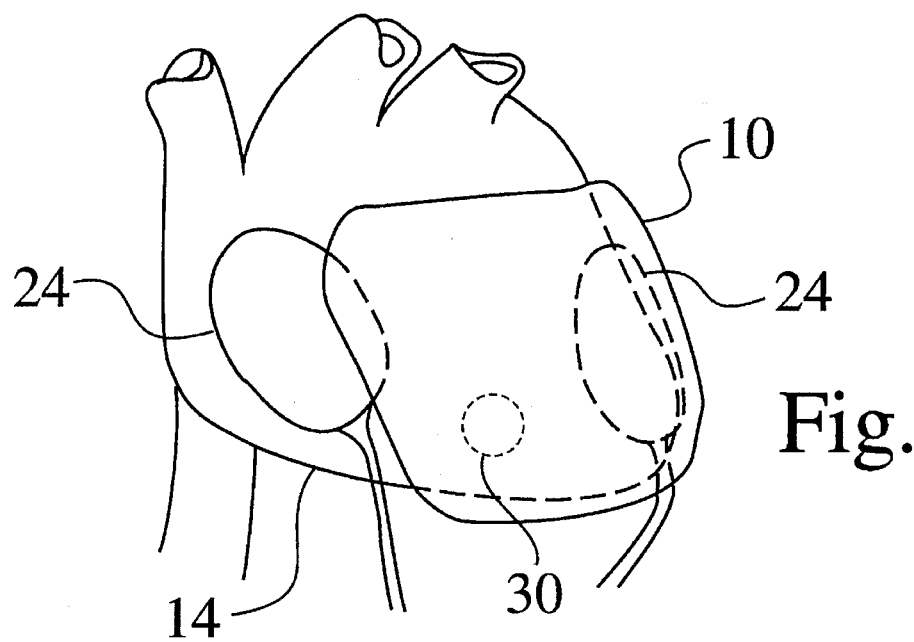
FIG. 4 shows an insulation device.
Figure 5:
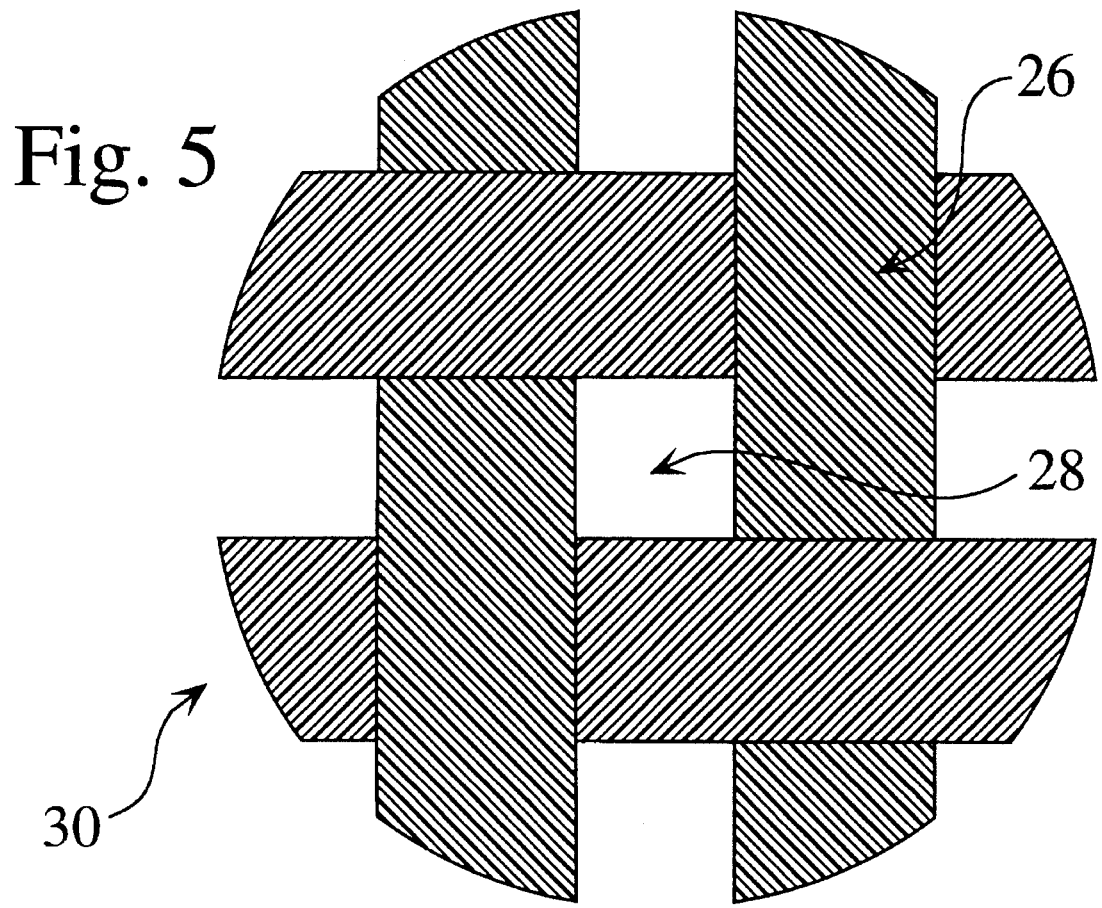
FIG. 5 is an enlarged sectional view of a portion of the insulation device of FIG. 4 comprising woven insulating material.

FIGS. 4 and 5 show an insulation device 10 and a detail view of a portion 30 of insulation device 10, respectively.

The insulation device 10 comprises woven strips of insulating material such as PTFE, silicone, or expanded PTFE, which form covered regions 26 and spaces 28. This structure is compliant, allows for fluid transport, and provides shielding effects. A mesh structure having a large proportion of covered regions 26 to spaces 28 has a greater insulating effect than one with a smaller proportion of covered regions to spaces. Such a mesh configuration may also be used to provide structures to the injectable liquid or gel described in connection with FIG. 2. This combination also serves to provide a greater insulative effect in regions having both the mesh substrate and the injected insulating material.

The principal advantage of the insulation device is that it forces current through the heart, thus increasing the current density and energy throughout the heart, to depolarize the greatest amount of cardiac tissue at the lowest possible voltage. The device may be positioned such that the body is selectively insulated from the heart; that is, it may not be necessary to completely surround the heart with insulation, but merely to insulate the portion where current flows to the adjacent body tissues.

In another embodiment, the insulation device contains a drug which elutes into the pericardial fluid and to adjacent tissues such as the pericardium or myocardium. The drug may be any suitable drug or combination of drugs intended to accomplish any desirable localized purpose, such as to counter thrombus formation, fibrosis, inflammation, poor myocardial perfusion, ischemia, arrhythmias, or any combination of these. As examples, the steroid dexamethasone sodium phosphate may be used for reducing fibrotic growth, or a growth factor may be used for introducing new capillary growth to increase perfusion of the myocardium.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. An implantable epicardial cardiac device for directing defibrillation electrical energy to a patient's heart consisting of electrical insulation which is permanently implantable to shield the body of said patient from at least a portion of said defibrillation electrical energy, wherein said insulation includes an outer edge and an aperture .apart from said outer edge, wherein some of said defibrillation electrical energy can pass from said patient's heart, through said aperture, to said patient's body.

2. The device of claim 1, wherein said aperture has a width of between about two and five centimeters.

3. The device of claim 1, wherein said aperture is positioned on said device such that said aperture is eccentric with respect to said outer edge of said insulation.

4. The device of claim 1, wherein said insulation includes a second aperture, whereby defibrillation energy applied from an external defibrillator to the patient can pass transthoracically to the patient's heart.

5. The device of claim 1, wherein said insulation is manufactured larger than intended for implant and comprises a material that can be trimmed by a physician during implant to fit said patient's heart for optimizing said shielding of said patient's body from said defibrillation electrical energy.

6. The device of claim 1, wherein said insulation is nonplanar.

7. The device of claim 1, wherein said insulation comprises an elastomeric material which is sufficiently compliant to stretch and contract with heart motion.

8. The device of claim 1, wherein said insulation comprises silicone rubber.

9. The device of claim 1, wherein said insulation comprises polytetrafluoroethylene.

10. The device of claim 9, wherein said insulation comprises expanded polytetrafluoroethylene.

11. The device of claim 2, wherein said insulation comprises a mesh of woven electrically insulating material.

12. An implantable epicardial cardiac device for directing defibrillation electrical energy to a patient's heart consisting of electrical insulation for implantation into the pericardial space of said patient's heart to shield said patient's body from at least a portion of said defibrillation electrical energy, wherein said insulation comprises a dispersion of silicone rubber particles in collagen glue.

13. An implantable epicardial cardiac device for directing defibrillation electrical energy to a patient's heart consisting of electrical insulation for implantation into the pericardial space of said patient's heart to shield said patient's body from at least a portion of said defibrillation electrical energy, wherein said insulation comprises a dispersion of polytetrafluoroethylene particles in collagen glue.

14. An implantable epicardial cardiac device for directing defibrillation electrical energy to a patient's heart consisting of electrical insulation for implantation into the pericardial space of said patient's heart to shield said patient's body from at least a portion of said defibrillation electrical energy, wherein said insulation comprises a dispersion of expanded polytetrafluoroethylene particles in collagen glue.

15. An implantable epicardial cardiac device for directing defibrillation electrical energy to a patient's heart consisting of electrical insulation for implantation into the pericardial space of said patient's heart to shield said patient's body from at least a portion of said defibrillation electrical energy, wherein said insulation comprises:

a mesh substrate; and collagen glue at least partially surrounding said mesh substrate.

16. A cardiac stimulation system kit, including:

an implantable pulse generator for generating defibrillation electrical energy;

at least one implantable defibrillation lead; and an implantable device consisting of insulation having a dielectric strength sufficient to shield the body from at least a portion of said defibrillation electrical energy.

17. The cardiac stimulation system kit of claim 16, wherein said at least one implantable defibrillation lead includes an endocardial right ventricular defibrillation lead.

18. The cardiac stimulation system kit of claim 16, wherein said at least one defibrillation lead includes a superior vena cava defibrillation lead.

19. The cardiac stimulation system kit of claim 16, wherein said at least one defibrillation lead includes an epicardial defibrillation lead.

20. The cardiac stimulation system kit of claim 16, wherein said at least one defibrillation lead includes a subcutaneous defibrillation lead and a second lead located proximate to the patient's heart.

21. A cardiac stimulation system kit including:

an implantable pulse generator for generating defibrillation electrical energy;

a first implantable subcutaneous defibrillation lead;

a second implantable defibrillation lead for placement proximate a patient's heart; and an implantable insulative device consisting of insulation having a dielectric strength sufficient to shield a patient's body from at least a portion of said defibrillation electrical energy; wherein said insulative device contains an aperture, said aperture allowing current flow between said subcutaneous defibrillation lead and said second lead located proximate said patient's heart.

22. A method of implanting an implantable defibrillation system in a patient comprising the steps of:

(a) providing a device consisting of insulation;

(b) positioning said insulation around a portion of the patient's heart;

(c) positioning at least two electrodes in or near the patient's heart;

(d) electrically coupling said electrodes to an implantable defibrillation pulse generator; and (e) implanting said implantable defibrillation pulse generator within the patient.

23. A method of implanting defibrillation electrodes in a patient comprising the steps of:

(a) providing a device consisting of insulation;

(b) positioning said insulation around a portion of the patient's heart;

(c) positioning at least two electrodes in or near the patient's heart; and (d) trimming said insulation.

24. A method of implanting defibrillation electrodes in a patient comprising the steps of:

(a) providing a device consisting of injectable insulating material;

(b) positioning said insulating material around a portion of the patient's heart by injecting said insulating material into the patient's pericardial space; and (c) positioning at least two electrodes in or near the patient's heart.

25. A method of implanting defibrillation electrodes in a patient comprising the steps of:

(a) injecting uncured material into the patient's pericardial space;

(b) allowing said material to cure into a compliant, solid, insulating form; and (c) positioning at least two electrodes in or near the patient's heart.

* * * * *